United States Patent
Takakura et al.

(10) Patent No.: US 10,126,276 B2
(45) Date of Patent: Nov. 13, 2018

(54) GAS CHROMATOGRAPH-MASS SPECTROMETER

(71) Applicant: SHIMADZU CORPORATION, Kyoto-shi, Kyoto (JP)

(72) Inventors: Masato Takakura, Kyoto (JP); Syuichi Kawana, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/021,959

(22) PCT Filed: Sep. 25, 2013

(86) PCT No.: PCT/JP2013/075852
§ 371 (c)(1),
(2) Date: Mar. 15, 2016

(87) PCT Pub. No.: WO2015/045028
PCT Pub. Date: Apr. 2, 2015

(65) Prior Publication Data
US 2016/0223500 A1    Aug. 4, 2016

(51) Int. Cl.
*G01N 30/28* (2006.01)
*G01N 30/32* (2006.01)
(Continued)

(52) U.S. Cl.
CPC ......... *G01N 30/32* (2013.01); *G01N 30/7206* (2013.01); *G01N 30/30* (2013.01);
(Continued)

(58) Field of Classification Search
CPC ..... G01N 2030/3084; G01N 2030/324; G01N 30/30; G01N 30/32; G01N 30/7206
See application file for complete search history.

(56) References Cited

U.S. PATENT DOCUMENTS 8,513,593 B2    8/2013  Quimby et al.
9,435,774 B2 *  9/2016  Kawana ................. G01N 30/38
(Continued)

FOREIGN PATENT DOCUMENTS

JP    60-149969 A    8/1985
JP    2000-304751 A   11/2000
(Continued)

OTHER PUBLICATIONS

International Search Report for PCT/JP2013/075852 dated Dec. 17, 2013.
(Continued)

*Primary Examiner* — Wyatt Stoffa
(74) *Attorney, Agent, or Firm* — Sughrue Mion, PLLC (57) ABSTRACT

A column protection gas supply channel (4) is connected to a channel (17) for carrier gas present between a sample vaporization chamber (12) and an MS section (2). During a standby, a column (11) may be protected on the downstream side of a merging section (16) of the column protection gas supply channel (4) and the channel (17) for carrier gas by supplying column protection gas through the column protection gas supply channel (4). At this time, there is remaining carrier gas in the channel (17) for carrier gas on the upstream side of the merging section (16). Accordingly, when carrier gas is then supplied at a time of start of an analysis, a certain amount of carrier gas is already present inside the channel (17). Therefore, the time required to completely replace the column protection gas in the channel (17) by the carrier gas is reduced, and the standby time until the start of the analysis may be reduced.

14 Claims, 5 Drawing Sheets

(51) Int. Cl.
    *G01N 30/72* (2006.01)
    *G01N 30/30* (2006.01)
(52) U.S. Cl.
    CPC ............... *G01N 2030/3038* (2013.01); *G01N 2030/3084* (2013.01); *G01N 2030/324* (2013.01)

(56) References Cited

U.S. PATENT DOCUMENTS

| | | | | |
|---|---|---|---|---|
| 2007/0184553 | A1* | 8/2007 | Hartlein | G01N 30/24 436/50 |
| 2010/0101304 | A1* | 4/2010 | McIntyre | G01N 30/7206 73/23.37 |
| 2011/0100093 | A1* | 5/2011 | Kawana | G01N 30/28 73/23.42 |
| 2012/0125444 | A1* | 5/2012 | Tipler | G01N 30/40 137/14 |
| 2013/0062515 | A1* | 3/2013 | Quimby | H01J 49/0027 250/282 |
| 2013/0125620 | A1* | 5/2013 | Ovadia | G01N 30/08 73/23.39 |
| 2016/0139089 | A1* | 5/2016 | Ovadia | G01N 30/08 73/23.39 |

FOREIGN PATENT DOCUMENTS

| | | |
|---|---|---|
| JP | 2009-128305 A | 6/2009 |
| JP | 2011-95072 A | 5/2011 |
| JP | 2013-44647 A | 3/2013 |
| JP | 2013061324 A | 4/2013 |

OTHER PUBLICATIONS

Communication dated Dec. 20, 2016 from the Japanese Patent Office in counterpart application No. 2015-538677.
Notification of Reasons for Refusal, dispatched Aug. 1, 2017, in corresponding JP Application No. 2015-538677, 9 pages in English and Japanese.

* cited by examiner

GAS CHROMATOGRAPH-MASS SPECTROMETER

CROSS REFERENCE TO RELATED APPLICATIONS

This application is a National Stage of International Application No. PCT/JP2013/075852filed Sep. 25, 2013, the contents of which are incorporated herein by reference in their entirety.

TECHNICAL FIELD

The invention relates to a gas chromatograph-mass spectrometer for performing mass spectrometry by introducing carrier gas containing sample components into a column, and by ionizing, inside a vacuum chamber, a sample component separated by the column.

BACKGROUND ART

A gas chromatograph-mass spectrometer (GC/MS) is provided with a gas chromatograph section and a mass spectrometry section. Sample components supplied to a column of the gas chromatograph section together with carrier gas are separated into each sample component in the process of passing through the column, and are sequentially lead to the mass spectrometry section and ionized, and mass spectrometry is thus performed (for example, see Patent Document 1).

Figure 4:
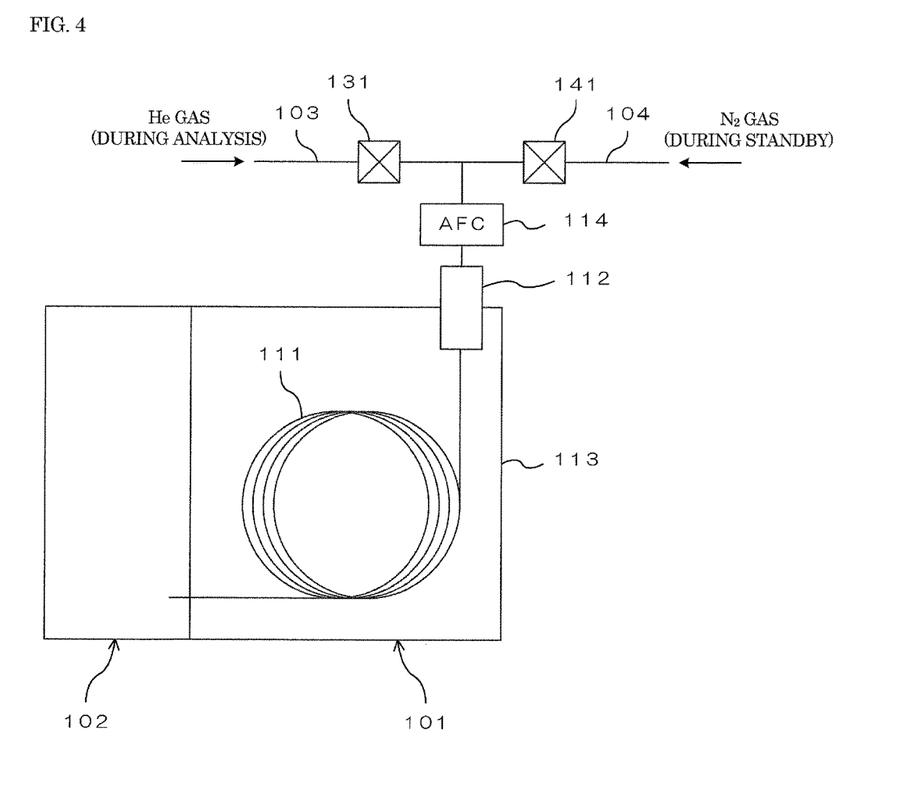
FIG. 4 is a schematic cross-sectional diagram showing an example configuration of a conventional gas chromatograph-mass spectrometer.

FIG. 4 is a schematic cross-sectional diagram showing an example configuration of a conventional gas chromatograph-mass spectrometer. This gas chromatograph-mass spectrometer is provided with a gas chromatograph section (GC section 101) and a mass spectrometry section (MS section 102).

The GC section 101 is provided with a column 111, a sample vaporization chamber 112, a column oven 113, and an AFC (Auto Flow Controller) 114, for example. A sample component is supplied, together with carrier gas, to the column 111 from the sample vaporization chamber 112. The column 111 is provided inside the column oven 113, and during an analysis, a sample component may be supplied to the column 111 while the column 111 is being heated by a heater (not illustrated) inside the column oven 113.

As the carrier gas, He gas is used, for example. Carrier gas may be supplied to the sample vaporization chamber 112 through the AFC 114, and during an analysis, the flow rate of the carrier gas that is supplied to the sample vaporization chamber 112 may be adjusted by the AFC 114.

The MS section 102 is provided with a vacuum chamber (not illustrated), and the inside of the vacuum chamber may be placed in a vacuum state. During an analysis, a sample component separated by the column 111 may be lead to the vacuum chamber in the vacuum state to be ionized, and the ions may be detected by an ion detector (not illustrated), and mass spectrometry may thus be performed.

According to such a gas chromatograph-mass spectrometer, if the power of the device is turned off after an analysis is completed, it takes time for the vacuum chamber of the MS section 102 to fall into a vacuum state at the time of turning on of the power for the next analysis. Accordingly, even if there is time from completion of an analysis until the next analysis, the device is often kept in a standby with the power being on.

However, if the device is kept in a standby for a long time in a state where the power is on but there is no flow of carrier gas, the temperature of an ion source of the MS section 102 may be increased, possibly causing deterioration of the column 111 (especially the part immediately before the MS section 102). Accordingly, during a standby, column protection gas is sometimes caused to flow inside the column 111 to protect the column 111.

As the column protection gas, $N_2$ gas is used, for example. In the example of FIG. 4, the column protection gas is supplied to the sample vaporization chamber 112 through the AFC 114, and is caused to flow from the sample vaporization chamber 112 into the column 111. On the upstream side of the AFC 114, an on-off valve 131 is provided on a channel 103 for the carrier gas (He gas), and an on-off valve 141 is provided on a channel 104 for the column protection gas ($N_2$ gas).

Accordingly, during an analysis, the carrier gas may be supplied to the column 111 through the sample vaporization chamber 112 by placing the on-off valve 131 in an open state and the on-off valve 141 in a closed state. On the other hand, during a standby, the column protection gas may be supplied to the column 111 through the sample vaporization chamber 112 by placing the on-off valve 131 in a closed state and the on-off valve 141 in an open state.

PRIOR ART DOCUMENTS

Patent Documents

Patent Document 1: JP 2013-44647 A

SUMMARY OF THE INVENTION

Problems to be Solved by the Invention

According to the conventional gas chromatograph-mass spectrometer as described above, the AFC 114, the sample vaporization chamber 112, and the column 111 are filled with the column protection gas during a standby. Therefore, at the time of starting an analysis after the standby, the analysis has to be started after the carrier gas is supplied and the column protection gas inside the AFC 114, the sample vaporization chamber 112, and the column 111 is replaced by the carrier gas.

However, in this case, due to the presence of dead volumes inside the AFC 114 and the sample vaporization chamber 112, there is a problem that replacement of gas inside the AFC 114, the sample vaporization chamber 112, and the column 111 takes time, and that the standby time until the start of an analysis is long.

Figure 5:
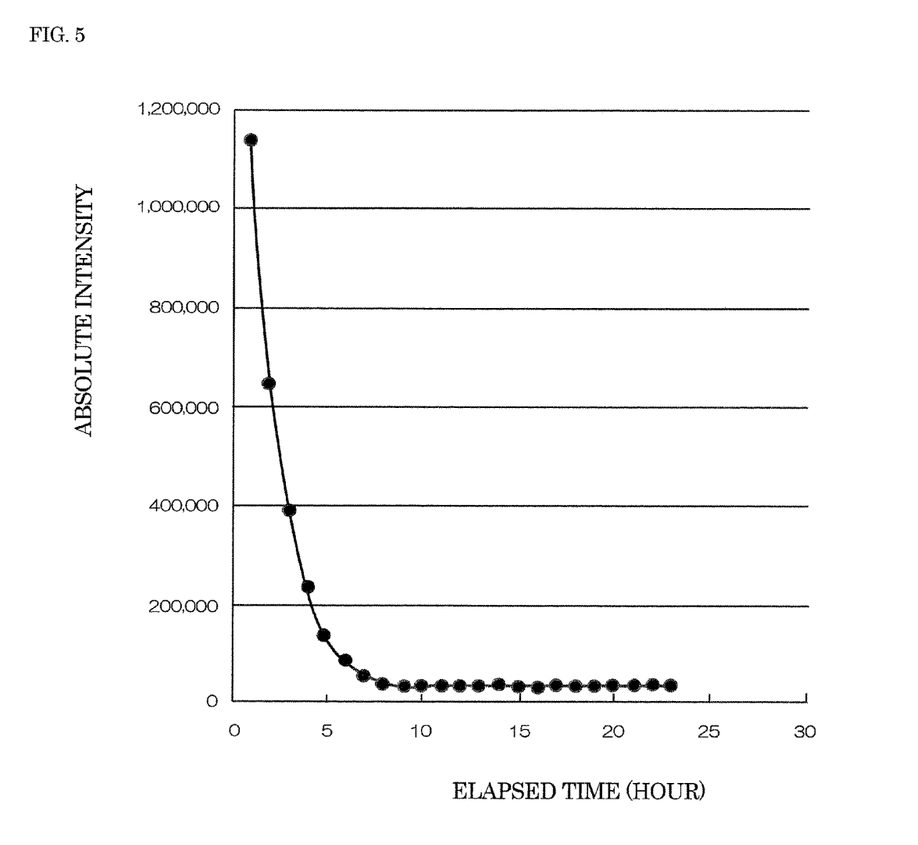
FIG. 5 is a diagram showing an example of a time required to replace the gas in a AFC, the sample vaporization chamber, and the column.

FIG. 5 is a diagram showing an example of a time required to replace the gas in the AFC 114, the sample vaporization chamber 112, and the column 111. FIG. 5 shows an example of a change over time in an absolute intensity of the $N_2$ gas (column protection gas) detected at the MS section 102 in a case where the $N_2$ gas inside the AFC 114, the sample vaporization chamber 112, and the column 111 is replaced by the He gas (carrier gas) at the time of start of an analysis.

As shown in FIG. 5, a long standby time is necessary to approximately completely replace the gas inside the column 111. In the case where an analysis is started before sufficient time has passed, there is remaining $N_2$ gas (column protection gas) in the column 111, and thus the accuracy of the analysis is possibly reduced.

The present invention has been made in view of the above circumstance, and has its object to provide a gas chromatograph-mass spectrometer that is capable of reducing a standby time until start of an analysis.

Means for Solving the Problems

A gas chromatograph-mass spectrometer according to the present invention includes: a sample vaporization chamber for vaporizing a sample; a column to which carrier gas containing a sample component is introduced from the sample vaporization chamber; a mass spectrometry section for performing mass spectrometry by ionizing, inside a vacuum chamber, a sample component separated by the column; a column protection gas supply channel connected to a channel for carrier gas present between the sample vaporization chamber and the mass spectrometry section, the column protection gas supply channel being for supplying column protection gas for protecting the column to inside the channel; and a gas flow rate adjustment section for adjusting a flow rate of gas in such a way that, during an analysis, the carrier gas containing a sample component flows into the mass spectrometry section, and during a standby, the column protection gas flows into the mass spectrometry section.

According to such a configuration, during a standby, by supplying the column protection gas through the column protection gas supply channel connected to the channel for carrier gas present between the sample vaporization chamber and the mass spectrometry section, the column may be protected on the downstream side of the merging section of the column protection gas supply channel and the channel for carrier gas. At this time, there is remaining carrier gas in the channel for carrier gas on the upstream side of the merging section.

Accordingly, when carrier gas is then supplied at the time of start of an analysis, a certain amount of carrier gas is already present inside the channel. Therefore, the time required to completely replace the column protection gas in the channel by the carrier gas is reduced, and the standby time until the start of the analysis may be reduced.

The column protection gas is desirably gas that is less expensive than the carrier gas. This allows a reduction in the running cost, because the column may be protected during a standby by using the column protection gas, which is less expensive, while suppressing consumption of the carrier gas.

The column protection gas supply channel is desirably connected to the channel on a downstream side of the column.

According to such a configuration, during a standby, there is remaining carrier gas on the upstream side of the column, and when carrier gas is then supplied at the time of start of an analysis, a large amount of carrier gas is already present inside the column. Therefore, the time required to completely replace the column protection gas in the channel by the carrier gas is further reduced, and the standby time until start of an analysis may be effectively reduced.

In this case, the column protection gas is supplied only to the downstream side of the column, but even with such a configuration, the column may be effectively protected because the temperature tends to be increased at the mass spectrometry section to which the downstream end of the column is connected and the column is easily deteriorated in the vicinity.

The gas chromatograph-mass spectrometer may further include a notification processing section for issuing, in a case where the flow rate of the carrier gas has reached or exceeded a predetermined value during the standby, a notification to an effect.

According to such a configuration, in a case where the carrier gas is flowing at a flow rate at or above the predetermined value during a standby when the column protection gas is being supplied through the column protection gas supply channel, the abnormality may be detected and a notification may be issued. Therefore, wasteful flow of the carrier gas may be prevented, and consumption of the carrier gas may be suppressed.

The gas chromatograph-mass spectrometer may further include: a column oven for heating the column; and a column temperature adjustment section for heating the column by the column oven during the analysis, and for reducing a temperature of the column during the standby compared to the temperature at a time of the analysis.

According to such a configuration, deterioration due to the carrier gas remaining in the channel for carrier gas being heated by the column oven during a standby and the temperature being excessively increased may be prevented. Also, wasteful consumption of power by the column oven during the standby may be prevented.

The gas flow rate adjustment section is desirably capable of causing an analysis to automatically start, by causing the carrier gas containing a sample component to flow into the mass spectrometry section, and after completion of the analysis, of causing shift to a standby state to automatically take place, by causing the column protection gas to flow into the mass spectrometry section.

According to such a configuration, an analysis may be automatically started, and also a standby state may be automatically reached after completion of the analysis and a state where the column is protected by the column protection gas will be reached, and the burden on a worker may be reduced.

Effects of the Invention

According to the present invention, since the time necessary to completely replace the column protection gas inside the channel by the carrier gas is reduced, the standby time until the start of an analysis may be reduced.

MODE FOR CARRYING OUT THE INVENTION

Figure 1:
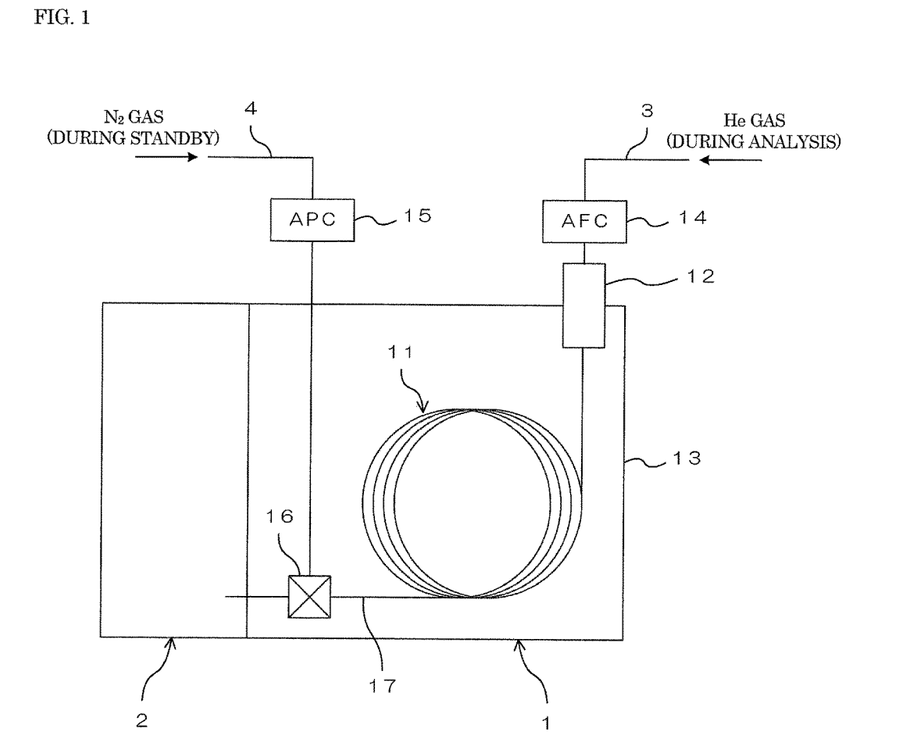
FIG. 1 is a schematic cross-sectional diagram showing an example configuration of a gas chromatograph-mass spectrometer according to an embodiment of the present invention.

FIG. 1 is a schematic cross-sectional diagram showing an example configuration of a gas chromatograph-mass spectrometer according to an embodiment of the present invention. This gas chromatograph-mass spectrometer (GC/MS) is provided with a gas chromatograph section (GC section 1) and a mass spectrometry section (MS section 2).

The GC section 1 is provided with a column 11, a sample vaporization chamber 12, a column oven 13, an AFC (Auto Flow Controller) 14, an APC (Auto Pressure Controller) 15, and a merging section 16, for example. The column 11 is formed as a capillary column, for example, and its upstream end is connected to the sample vaporization chamber 12 and its downstream end is connected to the MS section 2.

A liquid sample and carrier gas are supplied to the sample vaporization chamber 12, and sample components which are vaporized in the sample vaporization chamber 12 are then introduced into the column 11 together with the carrier gas. At the GC section 1, when the carrier gas containing sample components is introduced into the column 11, each sample component is separated in the process of the carrier gas passing through the column 11, and is sequentially led to the MS section 2 to be analyzed.

The column 11 is accommodated inside the column oven 13 together with a heater and a fan (neither is illustrated in the drawing), for example. The column oven 13 is for heating the column 11, and at the time of an analysis, an isothermal analysis of performing an analysis while maintaining a constant temperature inside the column oven 13, or a programmed temperature analysis of performing an analysis while gradually increasing the temperature inside the column oven 13 may be performed, for example, by appropriate driving of the heater and the fan.

As the carrier gas, He gas is used, for example. The carrier gas is supplied from a carrier gas supply channel 3 to the sample vaporization chamber 12 through the AFC 14. The AFC 14 is for adjusting the flow rate of the carrier gas, and at the time of an analysis, the flow rate of the carrier gas that is supplied from the carrier gas supply channel 3 to the sample vaporization chamber 12 is adjusted by the AFC 14 in such a way that the carrier gas flows through the column 11 at a constant flow rate.

According to the present embodiment, column protection gas for protecting the column 11 is supplied, during a standby at other than the time of analysis, into the column 11 through a column protection gas supply channel 4. Therefore, even in a case where, after completion of an analysis, standby is performed in a state where the power of the device is on, the column protection gas flows inside the column 11, and deterioration of the column 11 due to, for example, the temperature of an ion source of the MS section 2 increasing may be prevented.

As the column protection gas, $N_2$ gas is used, for example. The column protection gas is not limited to $N_2$ gas, but it is desirably gas which is less expensive than the carrier gas. That is, various types of gases may be used as the carrier gas and the column protection gas so long as the column protection gas is the less expensive of the combination. Since consumption of the carrier gas may be suppressed during a standby, and the column 11 may be protected by using the less expensive column protection gas, the running cost may be reduced.

The flow rate of the column protection gas that is supplied through the column protection gas supply channel 4 is adjusted by the APC 15. The APC 15 may supply the column protection gas at any flow rate by adjusting the supply pressure of the column protection gas inside the column protection gas supply channel 4.

The column protection gas supply channel 4 is connected to a channel 17 for carrier gas present between the sample vaporization chamber 12 and the MS section 2. More specifically, the column protection gas supply channel 4 is connected to the channel 17 for carrier gas, on the downstream side of the column 11. That is, the merging section 16 of the column protection gas supply channel 4 to the column 11 is provided to the column 11, at immediately before the MS section 2.

The GC section 1 may use a detector splitting system as the merging section 16. The detector splitting system configures a splitting section for splitting the column 11 on the downstream side and for leading sample components to a plurality of detectors to thereby analyze a plurality of types of sample components in parallel.

The MS section 2 is provided with a vacuum chamber and an ion detector (neither is illustrated in the drawing), for example. During an analysis, each sample component separated by the column 11 is lead into the vacuum chamber in a vacuum state. Then, each sample component which is ionized in the vacuum chamber is detected by the ion detector, thereby allowing mass spectrometry to be performed.

Figure 2:
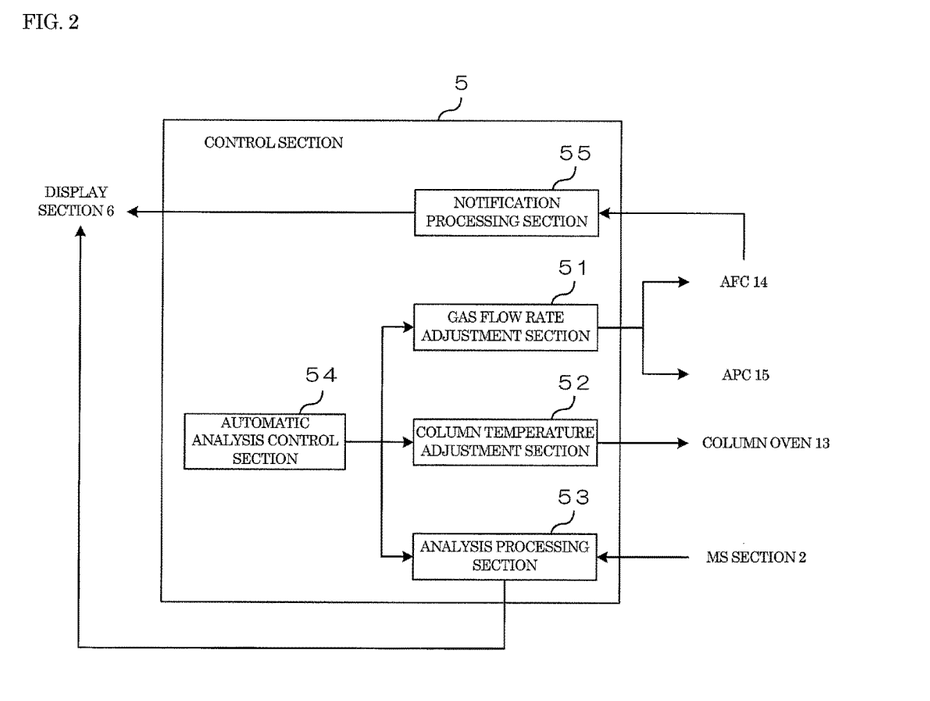
FIG. 2 is a block diagram showing an example of an electrical configuration of the gas chromatograph-mass spectrometer in FIG. 1.

FIG. 2 is a block diagram showing an example of an electrical configuration of the gas chromatograph-mass spectrometer in FIG. 1. The operation of the gas chromatograph-mass spectrometer is controlled by a control section 5 including a CPU (Central Processing Unit), for example.

The control section 5 functions as a gas flow rate adjustment section 51, a column temperature adjustment section 52, an analysis processing section 53, an automatic analysis control section 54, a notification processing section 55, and the like by the CPU executing programs. The gas chromatograph-mass spectrometer is provided with a display section 6 configured by a liquid crystal display, for example, in addition to the control section 5, and display on the display section 6 may be controlled by the control section 5.

The gas flow rate adjustment section 51 adjusts the flow rate of gas to be supplied to the column 11, by controlling the AFC 14 and the APC 15. Specifically, during an analysis, the carrier gas is supplied to the column 11 at a constant flow rate by the AFC 14 in a state where supply of the column protection gas from the column protection gas supply channel 4 is stopped by the APC 15. Accordingly, the carrier gas passes through the merging section 16 and flows into the MS section 2, and mass spectrometry is performed by the MS section 2 on the sample components contained in the carrier gas.

On the other hand, during a standby, the supply pressure of the column protection gas in the column protection gas supply channel 4 is adjusted by the APC 15 in such a way that the pressure, at the merging section 16, of the column protection gas acting on the side of the sample vaporization chamber 12 and the supply pressure of the carrier gas from the sample vaporization chamber 12 become equal. Accordingly, during the standby, a state where only the column protection gas flows into the MS section 2 through the merging section 16 and where the carrier gas does not flow into the MS section 2 is maintained.

In this manner, according to the present embodiment, the column 11 may be protected on the downstream side of the merging section 16 of the column protection gas supply channel 4 and the channel 17 for carrier gas during a standby, by the column protection gas being supplied through the column protection gas supply channel 4, which is connected to the channel 17 for carrier gas between the sample vaporization chamber 12 and the MS section 2. At this time, there is remaining carrier gas in the channel 17 for carrier gas on the upstream side of the merging section 16.

Accordingly, when the carrier gas is then supplied at the time of start of an analysis, a certain amount of carrier gas is already present inside the channel 17. Therefore, the time required to completely replace the column protection gas in the channel 17 by the carrier gas is reduced, and the standby time until the start of the analysis may be reduced.

Particularly, according to the present embodiment, because the column protection gas supply channel 4 is connected to the channel 17 on the downstream side of the column 11, there is, during a standby, remaining carrier gas on the upstream side of the column 11 (on the upstream side of the merging section 16). Therefore, when the carrier gas is then supplied at the time of start of an analysis, a large amount of carrier gas is already present inside the column 11. Accordingly, the time required to completely replace the column protection gas in the channel 17 by the carrier gas is further reduced, and the standby time until the start of an analysis may be effectively reduced.

In this case, the column protection gas is supplied only to the downstream side of the column 11, but even with such a configuration, the column 11 may be effectively protected because the temperature tends to be increased at the MS section 2 to which the downstream end of the column 11 is connected and the column 11 is easily deteriorated in the vicinity.

The column temperature adjustment section 52 adjusts the temperature of the column 11 by controlling the heater, the fan, and the like of the column oven 13. Specifically, during an analysis, the carrier gas inside the column 11 may be heated by heating the column 11 by the column oven 13. At the time of an isothermal analysis, the column temperature adjustment section 52 performs control in such a way that the temperature inside the column oven 13 becomes constant, and at the time of a programmed temperature analysis, the column temperature adjustment section 52 performs control in such a way that the temperature inside the column oven 13 is gradually increased.

On the other hand, during a standby, the column temperature adjustment section 52 controls the column oven 13 in such a way that the temperature of the column 11 becomes lower than that at the time of an analysis. At this time, a state where the column 11 is not heated is desirably reached by stopping driving of the column oven 13 (energization of the heater), but such a configuration is not restrictive, and a configuration according to which supply of current to the heater of the column oven 13 is reduced is also possible, for example.

Deterioration due to the carrier gas remaining in the channel 17 for carrier gas being heated by the column oven 13 during a standby and the temperature being excessively increased may thus be prevented. Also, wasteful consumption of power by the column oven 13 during the standby may be prevented.

The analysis processing section 53 may obtain a mass spectrum having a mass-to-charge ratio as the horizontal axis and a detection intensity as the vertical axis by performing mass spectrometry based on detection signals from the ion detector of the MS section 2. The mass spectrum obtained by the processing by the analysis processing section 53 may be displayed by the display section 6.

The automatic analysis control section 54 performs control for performing an automatic analysis by causing processing by the gas flow rate adjustment section 51, the column temperature adjustment section 52, the analysis processing section 53 and the like to be automatically performed. For example, at the time of an analysis, the analysis may be automatically started by the automatic analysis control section 54 controlling processing by the gas flow rate adjustment section 51 to cause carrier gas containing sample components to flow into the MS section 2.

During an analysis, the analysis is automatically performed by the automatic analysis control section 54 causing the analysis processing section 53 to process detection signals from the ion detector of the MS section 2. Then, after the analysis is completed, shift to a standby state automatically takes place by the automatic analysis control section 54 controlling processing by the gas flow rate adjustment section 51 in such a way as to cause the column protection gas to flow into the MS section 2.

If automatic analysis is performed by the automatic analysis control section 54, an analysis may be automatically started, and also a standby state may be automatically reached after completion of the analysis and a state where the column 11 is protected by the column protection gas will be reached, and the burden on a worker may be reduced.

The notification processing section 55 performs processing for notifying a worker of an abnormality, based on an input signal from the AFC 14. Specifically, the AFC 14 detects the flow rate of carrier gas passing through the AFC 14, and in the case where the flow rate of carrier gas reaches or exceeds a predetermined value during a standby, the notification processing section 55 notifies the worker by causing the display section 6 to perform display to the effect.

The predetermined value may be the same value or different values between a case where the carrier gas flows from the AFC 14 to the sample vaporization chamber 12 side and a case where the carrier gas flows from the sample vaporization chamber 12 side to the AFC 14. Also, the notification processing section 55 is not limited to the configuration according to which a worker is notified of an abnormality by display on the display section 6, and it is also possible to adopt a configuration according to which a worker is notified of an abnormality by sound or other means, for example.

Accordingly, in a case where the carrier gas is flowing at a flow rate at or above the predetermined value during a standby when the column protection gas is being supplied through the column protection gas supply channel 4, the abnormality may be detected and a notification may be issued. Therefore, wasteful flow of the carrier gas may be prevented, and thus consumption of the carrier gas may be suppressed.

Figure 3:
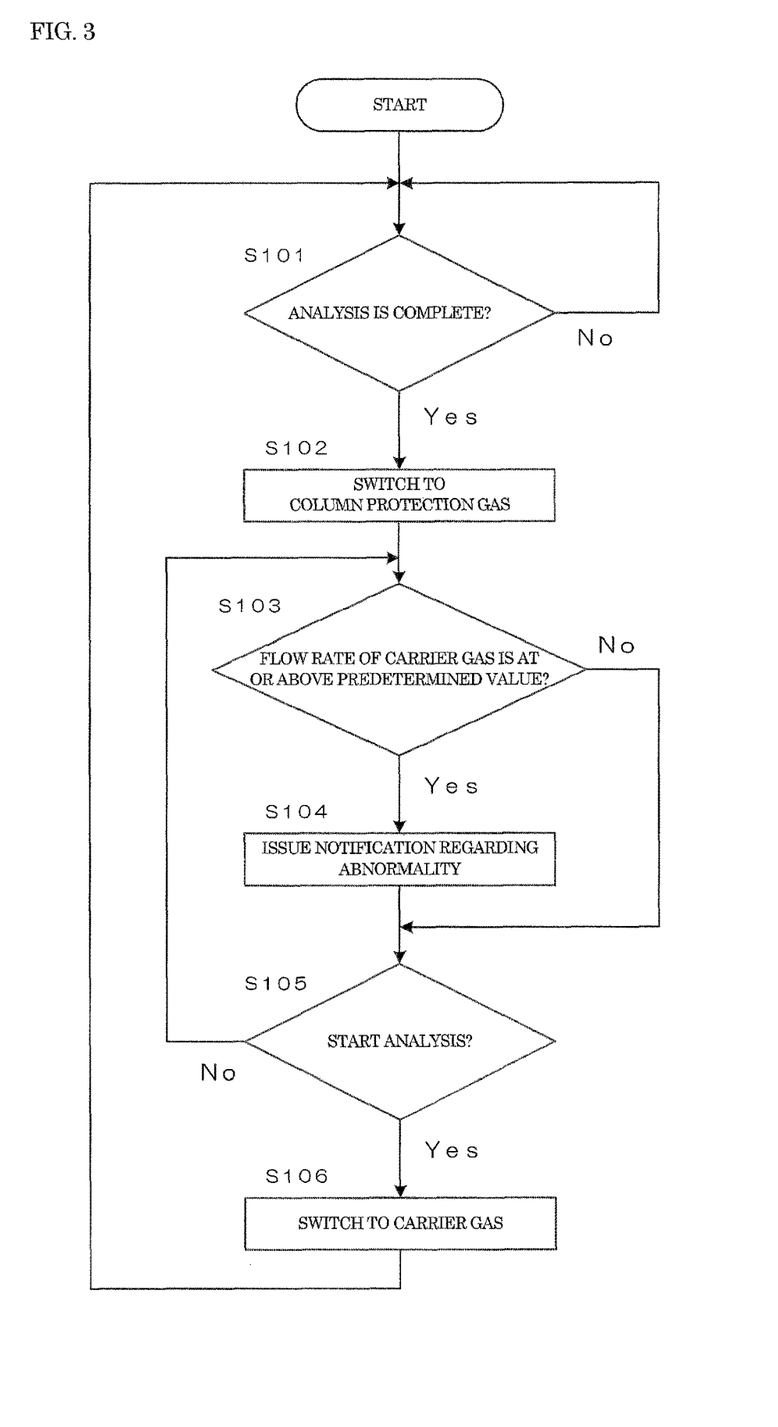
FIG. 3 is a flow chart showing an example of processing by a control section.

FIG. 3 is a flow chart showing an example of processing by the control section 5. During an analysis, the carrier gas is supplied from the carrier gas supply channel 3 to the MS section 2 through the column 11, but when the analysis is completed (Yes in step S101), switching is performed by the gas flow rate adjustment section 51 so that the column protection gas flows from the column protection gas supply channel 4 to the MS section 2 (step S102).

Then, whether the flow rate of the carrier gas reaches or exceeds the predetermined value is monitored (step S103) until the next analysis is started (until Yes in step S105 is reached). Then, in the case where the flow rate of the carrier gas reached or exceeded the predetermined value (Yes in step S103), a notification regarding an abnormality is issued by the notification processing section 55 (step S104).

In the case where an analysis is started (Yes in step S105), switching is performed by the gas flow rate adjustment section 51 so that the carrier gas flows from the carrier gas supply channel 3 to the MS section 2 (step S106), and processing in step S101 and later steps are performed again.

In the embodiment described above, a configuration is described where the merging section 16 of the column protection gas supply channel 4 to the channel 17 for carrier gas is provided on the downstream side of the column 11. However, such a configuration is not restrictive, and the merging section 16 may be provided at any position such as on the upstream side of the column 11 so long as the position is between the sample vaporization chamber 12 and the MS section 2.

Adjustment of the flow rate of the carrier gas does not necessarily have to be performed by the AFC 14, and it may be performed by using another mechanism such as an APC, for example. In the same manner, adjustment of the flow rate of the column protection gas does not necessarily have to be performed by the APC 15, and it may be performed by using another mechanism such as an AFC, for example.

The merging section 16 does not have to be provided with a detector splitting system, and gas flowing into the MS section 2 may be switched to the carrier gas or to the column protection gas by other configurations. In this case, a configuration according to which the gas is switched by pressure control is not restrictive, and it is possible to adopt a configuration according to which the channels for gases may be switched by using a channel switching mechanism such as a valve, for example.

DESCRIPTION OF REFERENCE SIGNS

1 GC section
2 MS section
3 carrier gas supply channel
4 column protection gas supply channel
5 control section
6 display section
11 column
12 sample vaporization chamber
13 column oven
14 AFC
15 APC
16 merging section
17 channel
51 gas flow rate adjustment section
52 column temperature adjustment section
53 analysis processing section
54 automatic analysis control section
55 notification processing section

The invention claimed is:

1. A gas chromatograph-mass spectrometer comprising:
a sample vaporization chamber for vaporizing a sample;
a column to which carrier gas containing a sample component is introduced from the sample vaporization chamber;
a mass spectrometry section for performing mass spectrometry by ionizing, inside a vacuum chamber, a sample component separated by the column;
a channel for carrier gas present between the sample vaporization chamber and the mass spectrometry section, the channel comprising the column;
a column protection gas supply channel connected to the channel for carrier gas present between the sample vaporization chamber and the mass spectrometry section, the column protection gas supply channel being for supplying column protection gas for protecting the column and the channel for carrier gas present between the sample vaporization chamber and the mass spectrometry section; and
a gas flow rate adjustment section implemented by a computer and configured to adjust a flow rate of gas in such a way that, during an analysis, the carrier gas containing a sample component flows into the mass spectrometry section and the column protection gas does not flow into the mass spectrometry section, and during a standby, the column protection gas flows into the mass spectrometry section and the carrier gas does not flow into the mass spectrometry section,
wherein the gas flow rate adjustment section adjusts the flow rate of gas in such a way that, during the standby, the pressure, at a merging section of the column protection gas supply channel to the column, of the column protection gas acting on the side of the sample vaporization chamber and the supply pressure of the carrier gas from the sample vaporization chamber become equal,
wherein during the standby the column is supplied with the column protection gas on a side of the column downstream from the merging section, and is supplied with the carrier gas on a side of the column upstream from the merging section,
wherein the column protection gas is a gas different from the carrier gas, and
wherein the gas flow rate adjustment section adjusts the flow rate of gas in such a way that the carrier gas is present in the column on the upstream side of the merging section while the column protection gas is supplied, and a certain amount of the carrier gas is already present inside the channel for carrier gas when the carrier gas is supplied at the time of a start of a next analysis.

2. The gas chromatograph-mass spectrometer according to claim 1, wherein the column protection gas supply channel is connected to the channel for carrier gas present between the sample vaporization chamber and the mass spectrometry section on a downstream side of the column.

3. The gas chromatograph-mass spectrometer according to claim 1, further comprising a notification processing section implemented by a computer and configured to issue, in a case where the flow rate of the carrier gas has reached or exceeded a predetermined value during the standby, a notification to an effect.

4. The gas chromatograph-mass spectrometer according to claim 1, further comprising:
a column oven for heating the column; and
a column temperature adjustment section implemented by a computer and configured to heat the column by the column oven during the analysis, and to reduce a temperature of the column during the standby compared to the temperature at a time of the analysis.

5. The gas chromatograph-mass spectrometer according to claim 1, wherein the gas flow rate adjustment section is configured to cause an analysis to automatically start, by causing the carrier gas containing a sample component to flow into the mass spectrometry section, and after completion of the analysis, to cause a shift to a standby state to automatically take place, by causing the column protection gas to flow into the mass spectrometry section.

6. The gas chromatograph-mass spectrometer according to claim 1, wherein the column protection gas is nitrogen gas ($N_2$), and the carrier gas is helium gas (He).

7. The gas chromatograph-mass spectrometer according to claim 1, wherein a downstream end of the column is connected to the mass spectrometry section.

8. A method for reducing the time from a standby time to a start time of an analysis for a gas chromatograph mass spectrometer, the gas chromatograph mass spectrometer comprising: a sample vaporization chamber for vaporizing a sample; a column to which carrier gas containing a sample component is introduced from the sample vaporization chamber; a mass spectrometry section for performing mass spectrometry by ionizing, inside a vacuum chamber, a sample component separated by the column; a channel for carrier gas present between the sample vaporization chamber and the mass spectrometry section, the channel comprising the column; and a column protection gas supply channel connected to the channel for carrier gas present between the sample vaporization chamber and the mass spectrometry section, the column protection gas supply channel being for supplying column protection gas for protecting the column and the channel for carrier gas present between the sample vaporization chamber and the mass spectrometry section; the method comprising:

adjusting a flow rate of gas in such a way that during an analysis, the carrier gas containing a sample component flows into the mass spectrometry section and the column protection gas does not flow into the mass spectrometry section, and during a standby, the column protection gas flows into the mass spectrometry section and the carrier gas does not flow into the mass spectrometry section, wherein the flow rate of gas is adjusted in such a way that, during the standby, the pressure, at a merging section of the column protection gas supply channel to the column, of the column protection gas acting on the side of the sample vaporization chamber and the supply pressure of the carrier gas from the sample vaporization chamber become equal, wherein during the standby the column is supplied with the column protection gas on a side of the column downstream from the merging section, and is supplied with the carrier gas on a side of the column upstream from the merging section, wherein the column protection gas is a gas different from the carrier gas, and wherein the flow rate of gas is adjusted in such a way that the carrier gas is present in the column on the upstream side of the merging section while the column protection gas is supplied, and a certain amount of the carrier gas is already present inside the channel for carrier gas when the carrier gas is supplied at the time of a start of a next analysis.

9. The method according to claim 8, wherein the column protection gas supply channel of the gas chromatograph mass spectrometer is connected to the channel for carrier gas present between the sample vaporization chamber and the mass spectrometry section on a downstream side of the column.

10. The method according to claim 8,
wherein the method further comprises:
issuing, in a case where the flow rate of the carrier gas has reached or exceeded a predetermined value during the standby, a notification to an effect.

11. The method according to claim 8, wherein the gas chromatograph mass spectrometer further comprises:
a column oven for heating the column; and
a column temperature adjustment section;
wherein the method further comprises:
using the column oven to heat the column during analysis; and
using the column oven to reduce a temperature of the column during the standby compared to the temperature at a time of the analysis.

12. The method according to claim 8, wherein the method further comprises:
automatically starting an analysis by causing the carrier gas containing a sample component to flow into the mass spectrometry section; and
automatically shifting the gas chromatograph mass spectrometer to a standby state by causing the column protection gas to flow into the mass spectrometry section.

13. The method according to claim 8, wherein the column protection gas is nitrogen gas ($N_2$) and the carrier gas is helium gas (He).

14. The method according to claim 8, wherein a downstream end of the column is connected to the mass spectrometry section.

* * * * *